United States Patent [19]

Evans

[11] 4,018,217
[45] Apr. 19, 1977

[54] ARM AND HAND REST DEVICE FOR MICROSURGERY

[76] Inventor: Daniel R. Evans, 2005 Valparaiso St., Valparaiso, Ind. 46384

[22] Filed: Nov. 20, 1975

[21] Appl. No.: 633,616

[52] U.S. Cl. .......................... 128/1 R; 128/303 R; 248/118; 248/118.3; 248/405; 269/328
[51] Int. Cl.² ...................... A61B 19/00; B68G 5/00
[58] Field of Search ................. 269/322, 327, 328; 248/118, 118.1, 118.3, 405; 108/43, 92; 128/1 R, 20, 132–134, 303 R

[56] References Cited

UNITED STATES PATENTS

| 585,424 | 6/1897 | Bolens | 248/405 |
| 1,135,155 | 4/1915 | Blundell | 248/118.3 |
| 1,230,873 | 6/1917 | Crossley | 128/20 |
| 2,963,247 | 12/1960 | Collier et al. | 248/81 |
| 3,169,744 | 2/1965 | Nocek et al. | 248/405 |
| 3,557,791 | 1/1971 | Dutty | 128/303 R |

FOREIGN PATENTS OR APPLICATIONS 178,046  2/1966  U.S.S.R. ............................ 269/328

Primary Examiner—Dalton L. Truluck
Attorney, Agent, or Firm—Marmaduke A. Hobbs

[57] ABSTRACT

An arm and hand rest device for performing microsurgery, such as an eye operation, on a patient lying on an operating table, the device having a board placed on the operating table beneath the upper body portion of the patient so that the weight of the patient will hold the device firmly in place. Two tables are disposed at the head end of the board and each includes a platform on which the hands and arms are rested while the surgeon uses a scalpel or other instrument in performing the operation. The tables are spaced from one another to define the area in which the patient's head is placed for the operation, and the platforms are adjustable vertically and have projections at the top end extending toward one another.

6 Claims, 7 Drawing Figures

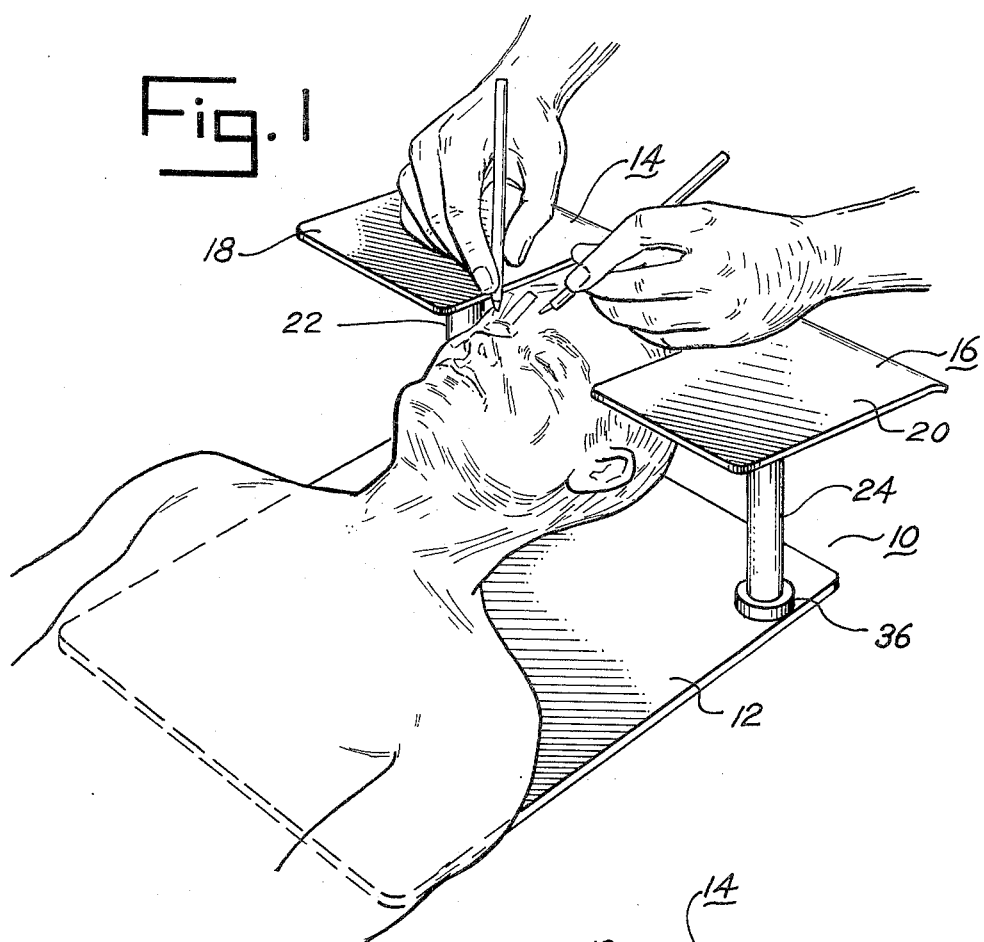
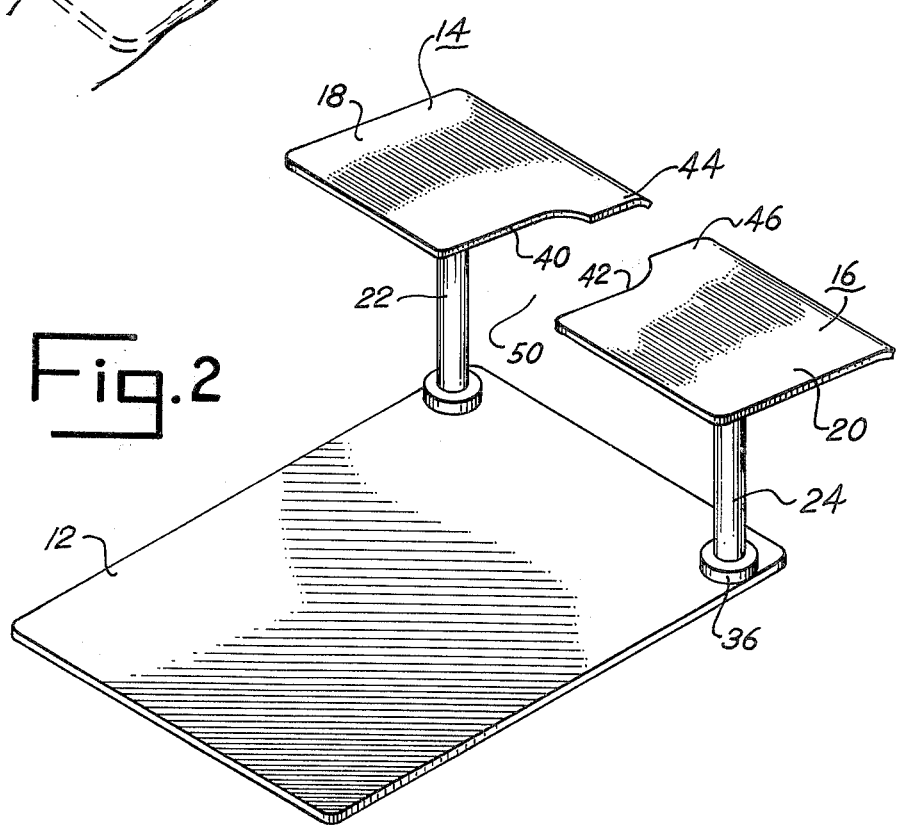

ARM AND HAND REST DEVICE FOR MICROSURGERY

When a physician performs eye surgery and similar delicate operations, it is important that the hand holding the scalpel or other surgical instrument has a firm support throughout the operating procedure to permit small and precise incisions to be made. In the past, various hand rests or supports have been used, but these have often involved the practice of utilizing standard operating table equipment or an improvision of equipment intended for other types of surgical operations. The standard or improvised equipment has generally been unsatisfactory for the type of microsurgery performed on an eye, and could result in failure to perform the required or proper incisions or might result in injury to the patient and/or an unsuccessful operation. It is therefore one of the principal objects of the present invention to provide an arm and hand rest for use by a physician in performing microsurgery, which will give firm and reliable support to the arm and hand and which can be easily and precisely adjusted to provide the optimum position for the physician's hand or hands while using a scalpel or other surgical instrument.

Another object of the invention is to provide a relatively simple, easy to use physician's hand support or rest which can be readily adapted to various operating tables without the use of a separate floor stand or stands, and without the use of fixtures or attachments on the operating table for holding the hand rest, and which can be used with standard operating tables and conveniently adjusted to the size of the patient and to the location of the part on which the operation is to be performed.

Still another object of the invention is to provide a supporting device for the hands of a physician in performing eye surgery and other delicate operations, which is held in place by the weight of the patient's body and which can conveniently be shifted to place the support in the most advantageous position for any particular step in the operating procedure.

A further object is to provide a hand rest supporting structure of the aforesaid type in which a rest may be provided on one or both sides of the patient's head, and may be adjusted vertically independently or one another to obtain the position most satisfactory for the operating procedure.

Additional objects and advantages of the present invention will become apparent from the following description and accompanying drawings, wherein:

FIG. 1 is a perspective view of a hand rest device for microsurgery, embodying the present invention, the view illustrating the manner in which it is used;

FIG. 2 is a perspective view of the hand rest device similar to that shown in FIG. 1, but without illustrating the use;

Figure 3:
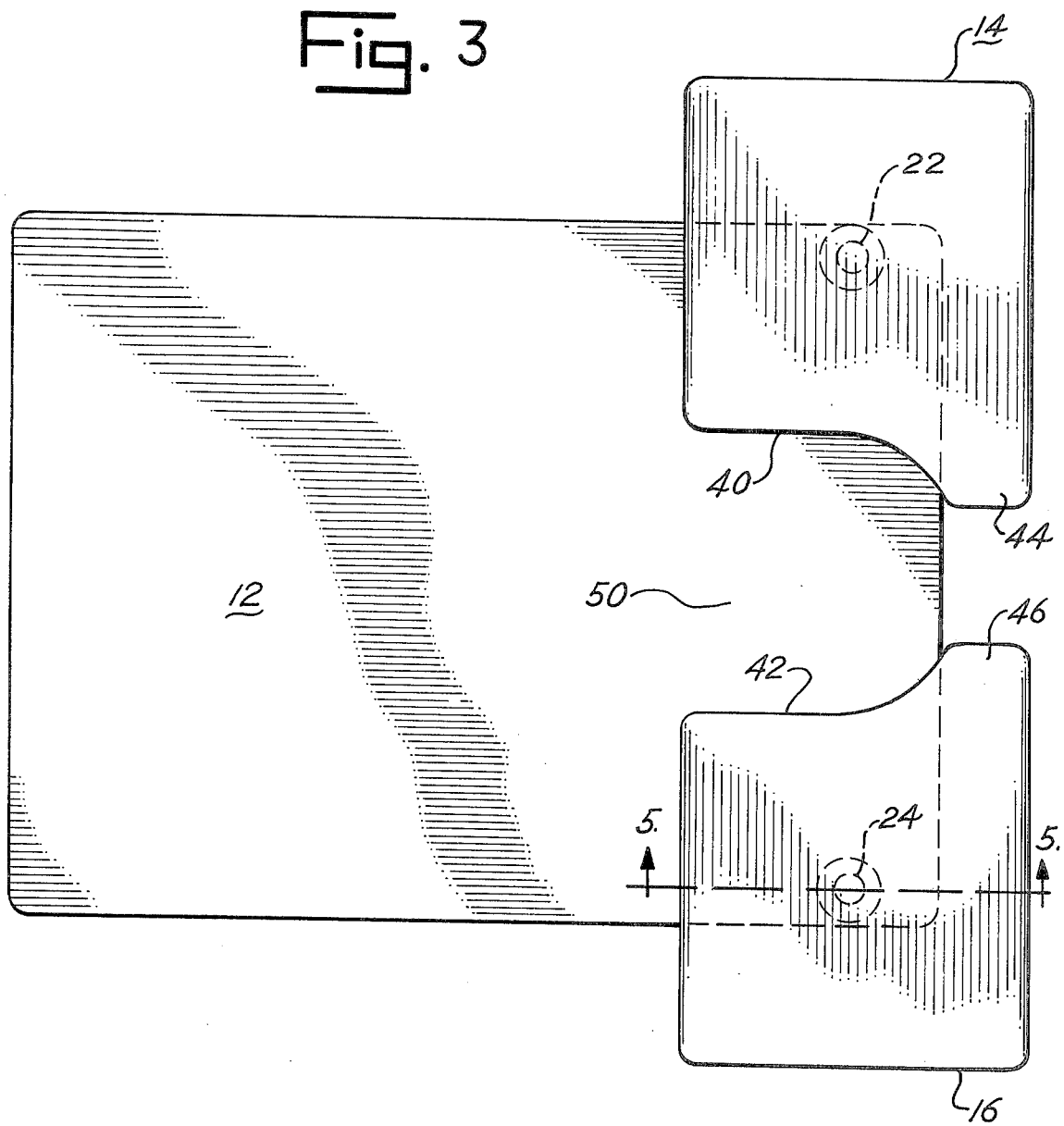
FIG. 3 is a top plan view of the hand rest device shown in FIG. 1.
Figure 4:
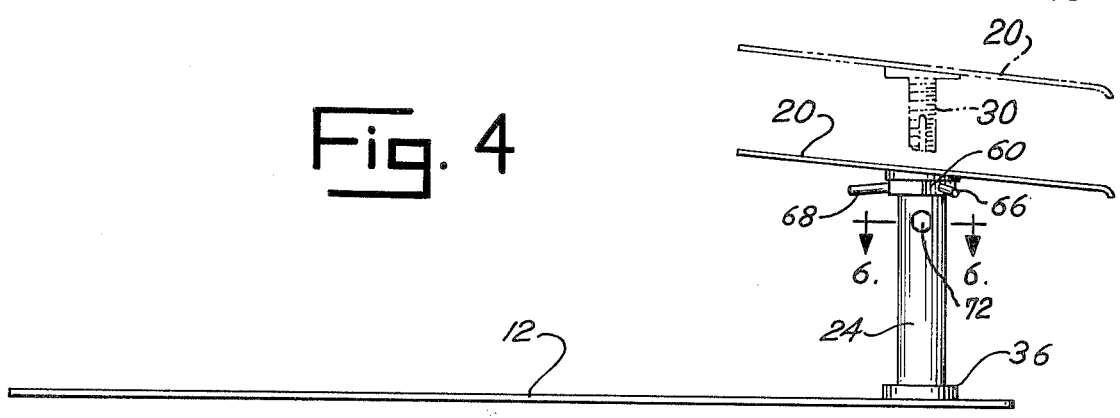
FIG. 4 is a side elevational view of the hand rest device shown in the preceding figures, illustrating the manner in which the hand rest is adjusted.
Figure 5:
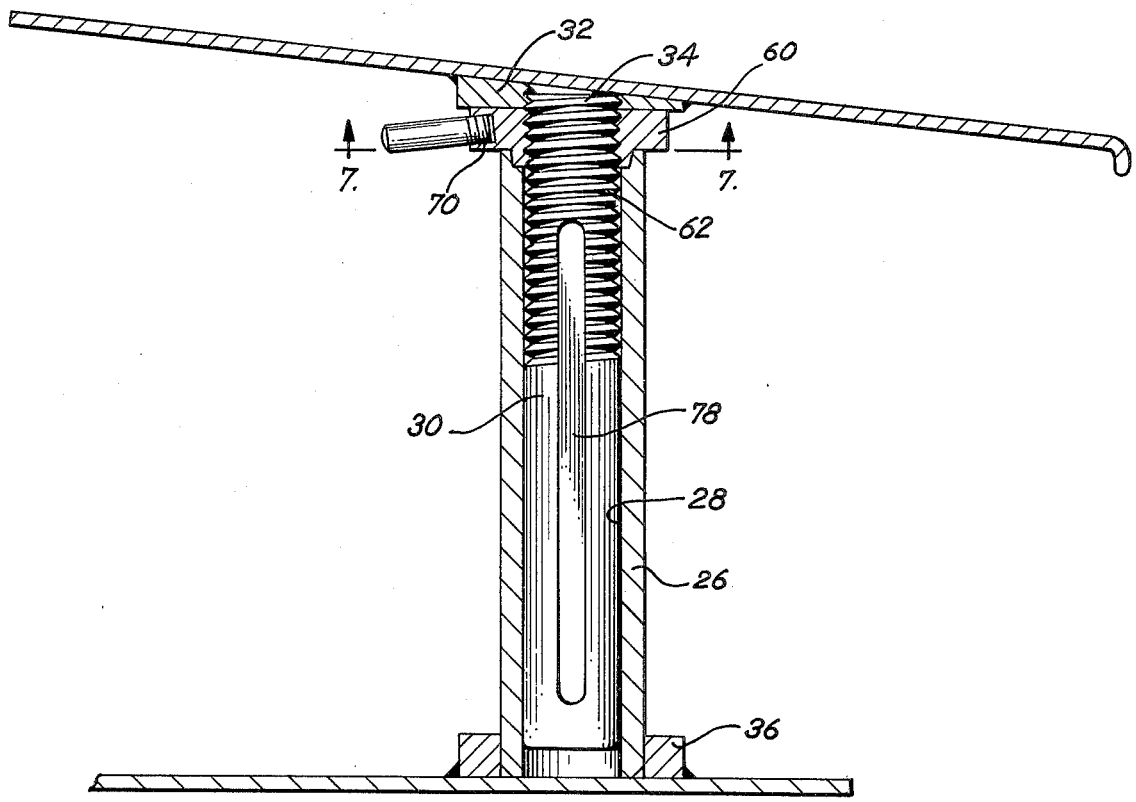
FIG. 5 is an enlarged, fragmentary cross sectional view of the hand rest device shown in the preceding figures, the section being taken on line 5 — 5 of FIG. 3.
Figure 6:
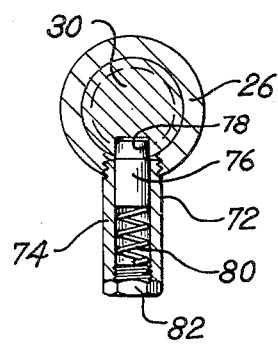
FIG. 6 is an enlarged, fragmentary cross sectional view of part of the adjustment means for the hand rest device shown in the preceding figures, the section being taken on line 6 — 6 of FIG. 4.
Figure 7:
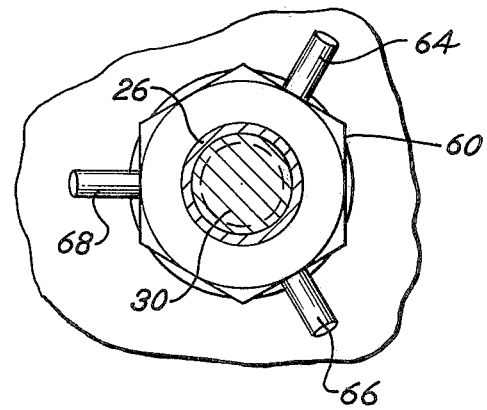
FIG. 7 is an enlarged fragmentary cross sectional view of another part of the adjustment mechanism, the section being taken on line 7 — 7 of FIG. 5.

Referring more specifically to the drawings and to FIG. 1 in particular, numeral 10 indicates generally the hand rest device for microsurgery, embodying the present invention, the figure illustrating the manner in which the device is used. The device includes a board 12 which is slipped under the patient as the patient lies on his back on an operating table and is held firmly in place by the weight of the patient's head and shoulders resting on the board. While this is the preferred way of holding the device in a firm position on the operating table, it may be used in other ways, such as by securing it to the operating table with clamps or fixtures; however, the manner illustrated in the drawings is the preferred way of using the device since it permits adjustment of the device with respect to the patient's body and head, either before or during the operation, and also easy removal of the device from the operating table after the operation has been completed, without appreciably disturbing the patient. The board may be varied in size, possibly extending it further down the patient's body, and may be wider or narrower if desired; however, it is preferred that it be at least as wide as the patient's body to avoid any discomfort which might result from the side edges of the board engaging the patient's body.

Mounted on the upper end of the board are two hand rest tables, indicated generally by numerals 14 and 16, the tables having platforms 18 and 20 supported by legs 22 and 24, respectively. The legs are essentially of the same construction, and each consists of a tubular or cylindrical member 26 having a cylindrical bore 28 axially disposed therein, and the respective platform is connected to a shaft 30 disposed in bore 28 and movable axially therein, as will be more fully explained hereinafter. The upper end of shaft 30 is connected to the respective platform by a boss 32 which is welded or otherwise secured to the underside of the respective platform and to the top end 34 of the shaft, either by a welded or threaded joint. The respective platform is thus rigidly secured to the upper end of shaft 30 and is held firmly in place thereby. The cylindrical member 26 is secured to the head end of board 12 by a collar 36 adjoined to the board by welding, soldering or other suitable securing means. The parts thus far described are preferably constructed of aluminum alloy; however, other materials such as plastic or wood, where suitable, may be used in the construction of the device. While the board 12 is shown lying flat beneath the patient, for convenience in describing the device, the end of the platform beneath the patient is referred to as the lower or bottom end and the end of board 12 on which the tables are mounted is referred to herein as the head or upper end.

Platform 18 of table 14 is provided with a recessed inner edge 40 and platform 20 with a recessed inner edge 42, in effect, providing inwardly extending projections 44 and 46 which provide an area indicated generally by number 50 under which the patient's head is placed in preparation for the operation. Thus, the two platforms 18 and 20 with inward extensions 44 and 46 provide an effective support for the arm and hand of the surgeon performing the operation, as illustrated in FIG. 1.

In each table, shaft 30 is adjusted vertically in member 26 by a nut 60 engaging threads 62 in the upper end of the shaft. The nut rests on the upper end of member 26 and is provided with operating pins 64, 66 and 68 disposed around the periphery and secured thereto by being threadedly received in respective bores 70 in the nut. The shaft and platform are prevented from rotating with respect to legs 22 and 24 by a detent mechanism indicated generally by numeral 72 and having a cylindrical housing 74, and a pin 76, the inner end of which seats in a longitudinal groove 78 in the side of shaft 30, the pin being yieldably held in the groove by a spring 80 reacting between the end of the pin and a cap 82 threadedly received in the end of housing 74. Thus, when nut 60 is rotated to make a vertical adjustment of the respective platforms 18 and 20, the shaft is prevented from turning, and hence is moved upwardly or downwardly through the nut as the nut is rotated.

In the use and operation of the present hand rest device for performing eye surgery or microsurgery of the patient's head, the board 12 is placed on the operating table and the patient lies on the board with his head generally disposed in area 50 between and beneath the inner edges 40 and 42 of platforms 18 and 20. This permits the surgeon to conveniently reach the patient's eye while resting his hands on the respective tables. Since the device is movable with respect to the patient's body, either table can be moved toward or away from the patient's head, thus providing effective adjustment for optimum operating conditions. After the patient has been placed on the board with his head between the two tables, either or both of the tables may be adjusted to provide the most suitable elevation with respect to the patient's eye for performing the operation, this vertical adjustment being accomplished by the rotation of nut 60 on the upper end of cylindrical member 26 of the respective legs 22 or 24. The device, being held by the weight of the patient on board 12 remains firmly in place throughout the operation, thus giving stable and dependable support to the surgeon's hands and arms while performing the operation. In the use illustrated in the drawings, both tables are shown being used, and this normally would be the practice; however, under special circumstances, one of the platforms may be removed by lifting shaft 30 from cylindrical member 26 after the detent has been withdrawn from slot 78, or, if desired, the device may be constructed so that member 26 is merely seated in collar 36, without being secured therein, thus permitting the entire table to be lifted from the collar and hence removed from the board.

The description herein has referred principally to the performing of surgery on the eye; however, the arm and hand rest device can be used effectively in performing other types of surgery on a patient's head without making any changes in the construction of the device. While only one embodiment of the present hand rest device for microsurgery has been described in detail herein, various changes and modifications may be made without departing from the scope of the invention.

I claim:

1. An arm and hand rest device for performing microsurgery on a patient lying on an operating table, comprising a horizontally disposed board for insertion between the patient's body and the operating table for retaining the device in a desired position with relation to the patient's body, a first table mounted on one end of said board and projecting upwardly therefrom and having an arm and hand rest at the top located in a position in close proximity to the patient's head when the operation is being performed, a second table mounted on said board in spaced relation to said first mentioned table and having an arm and hand rest at the top and, with the first table, defining an area for the patient's head, and means for vertically adjusting said tables to different levels relative to one another.

2. An arm and hand rest device for microsurgery as defined in claim 1 in which said arm and hand rest on each table consists of a substantially flat, horizontally disposed platform.

3. An arm and hand rest device as defined in claim 1 in which the means for adjusting the vertical height of the arm and hand rest includes a tubular member, a shaft disposed in said tubular member supporting said arm and hand rest and having a threaded section thereon near the top thereof, and a nut on said shaft engaging the upper end of said tubular member for vertically positioning said arm and hand rest.

4. An arm and hand rest device as defined in claim 1 in which at least one of said arm and hand rests consists of a flat substantially horizontal platform for supporting the surgeon's hand.

5. An arm and hand rest device as defined in claim 2 in which the facing edges of said platforms have projections extending toward one another at the edge of the platform near the adjacent end of the board to form a general contour between the boards corresponding to the shape of the patient's head while the patient is lying on his back.

6. An arm and hand rest device as defined in claim 1 in which the means for adjusting the vertical height of the arm and hand rests includes a tubular member, a shaft disposed in said tubular member supporting said arm and hand rest and having a threaded section thereon near the top thereof, and a nut on said shaft engaging the upper end of said tubular member for vertically positioning said arm and hand rest.

* * * * *